United States Patent [19]

Jaeger et al.

[11] Patent Number: 5,055,784
[45] Date of Patent: Oct. 8, 1991

[54] BRIDGELESS SYSTEM FOR DIRECTLY MEASURING COMPLEX IMPEDANCE OF AN EDDY CURRENT PROBE

[75] Inventors: Douglas J. Jaeger; Howard P. Groger, both of Radford, Va.

[73] Assignee: American Research Corporation of Virginia, Radford, Va.

[21] Appl. No.: 504,698

[22] Filed: Apr. 5, 1990

Related U.S. Application Data

[63] Continuation of Ser. No. 129,144, Dec. 7, 1987, abandoned.

[51] Int. Cl.[5] ............ G01R 33/12; G01R 27/02; G01N 27/90
[52] U.S. Cl. ............... 324/233; 324/234; 324/238; 324/607; 324/654; 364/482
[58] Field of Search .......... 324/233, 234, 236–241, 324/607, 649, 654; 364/482, 483

[56] References Cited

U.S. PATENT DOCUMENTS

| 2,535,608 | 12/1950 | Smith | 324/59 |
|---|---|---|---|
| 2,595,675 | 5/1952 | Jaynes | 324/57 R |
| 3,159,784 | 12/1964 | Haslett et al. | 324/238 X |
| 3,234,461 | 2/1966 | Trent et al. | 324/234 X |
| 3,281,681 | 10/1966 | Stevenson | 324/57 R X |
| 3,284,705 | 11/1966 | Dobson | 324/57 R |
| 3,434,048 | 3/1969 | Law et al. | 324/239 |
| 3,619,771 | 11/1971 | Hentschel | 324/239 |
| 3,970,925 | 7/1976 | Procter et al. | 324/59 X |
| 3,984,768 | 10/1976 | Staples | 364/482 X |
| 4,030,026 | 6/1977 | Payne | 324/329 |
| 4,059,795 | 11/1977 | Mordwinkin | 324/233 |
| 4,207,520 | 6/1980 | Flora et al. | 324/238 |
| 4,230,987 | 10/1980 | Mordwinkin | 324/236 |
| 4,303,885 | 12/1981 | Davis et al. | 324/237 |
| 4,383,218 | 5/1983 | Hansen et al. | 324/225 |
| 4,450,405 | 5/1984 | Howard | 324/234 |
| 4,458,196 | 7/1984 | Goyal et al. | 324/649 |
| 4,486,713 | 12/1984 | Gifford | 324/329 |
| 4,495,587 | 1/1985 | Plante et al. | 364/507 |
| 4,496,904 | 1/1985 | Harrison | 324/227 |
| 4,506,225 | 3/1985 | Loveless et al. | 324/334 |
| 4,556,846 | 12/1985 | D'Hondt | 324/238 |
| 4,564,809 | 1/1986 | Huschelrath et al. | 324/225 |
| 4,629,985 | 12/1986 | Papadimitriou et al. | 324/233 X |
| 4,651,093 | 3/1987 | Detriche et al. | 324/238 X |
| 4,672,501 | 6/1987 | Bilac et al. | 364/483 X |
| 4,763,071 | 8/1988 | McGee et al. | 324/233 |
| 4,799,011 | 1/1989 | Muller | 324/233 |

FOREIGN PATENT DOCUMENTS

| 0014729 | 9/1980 | European Pat. Off. | |
| 0228910 | 10/1985 | German Democratic Rep. | 324/59 |
| 2187558 | 9/1987 | United Kingdom | 324/232 |

OTHER PUBLICATIONS

Marvin et al., "Circuit for Remote Measurement of . . . or Admittance", Western Electric Tech. Digest, No. 14, Apr. 1969, pp. 11, 12.

Primary Examiner—Gerard R. Strecker
Attorney, Agent, or Firm—Dickstein, Shapiro & Morin

[57] ABSTRACT

An all digital eddy current measurement system is described and illustrated in which an eddy current probe is driven by a driving signal and voltage signals representing the current through and voltage across the probe coil are used to calculate the magnitude and phase angle of a complex probe impedance. Digitization of the voltage signals is controlled by a control logic system which is run separately from but initiated by a microprocessor, the latter of which functions to analyze the acquired data and calculate impedance magnitude and phase angle values therefrom.

24 Claims, 8 Drawing Sheets

BRIDGELESS SYSTEM FOR DIRECTLY MEASURING COMPLEX IMPEDANCE OF AN EDDY CURRENT PROBE

This application is a continuation of application Ser. No. 07/129,144, filed Dec. 7, 1987, abandoned.

BACKGROUND OF THE INVENTION

1. Field of the Invention

The present invention relates to the field of non-destructive testing, and, more particularly, to the field of non-destructive testing using eddy current measuring systems which rely on the interaction of time varying electromagnetic fields with a conductive specimen under test.

2. Discussion of the Prior Art

The use of eddy current techniques for non-destructive testing of conductive specimens is well known in the art. Typically, systems employing eddy current techniques generate electromagnetic fields at a probe which induce eddy currents in a test specimen, which set up their own electromagnetic field distribution which couples with the initial excitation field produced by the probe coil. This coupling effectively transfers the impedance of the test specimen to the probe excitation coil so the changes in the test specimen which affect the transfer impedance may be detected at the excitation coil. The transfer impedance is affected by a number of factors including the conductivity properties of the test specimen, magnetic permeability, and geometrical factors such as proximity of the excitation coil to the specimen.

Generally, non-distructive test systems using eddy current techniques have been largely used for defect detection and characterization, and for materials sorting and sizing applications. However, any material characteristic which affects the transferred impedamce, either directly or indirectly, can be detected and measured by the eddy current probe. Thus, apart from the obvious direct measurement of speciment conductivity and magnetic properties, eddy current techniques have also been used to measure corrosion thickness, hardness, heat treating, and residual stress levels. Measurement of such mechanical properties are indirect in that the property change affects the metallurgical behavior of the material which results in changes in conductivity and permeability, thereby in turn alternatinng the measured impedance of the eddy current test probe.

Eddy current techniques for non-destructive testing rely on an accurate measurement of probe impedance as this is the parameter which is directly affected by defects or changes in material properties. At present, there are two major techniques by which eddy current probe signals are acquired and analyzed, respectively employing impedance bridges, and quadrature synthesis. However, neither of these techniques provides a direct indication of probe impedance, but only provides measures of relative changes in the probe impedance with location or time.

In addition, with impedance bridge techniques, all processing is performed with analog circuits, thus reducing accuracy and lowering the signal-to-noise ratio of the final result.

Quadrature synthesis techniques do not use an impedance bridge, but require the creation of two quadrature phase signals representing the voltage waveform driving a probe. Various combinations of the two phase shifted waveforms are used with an output signal from the probe to create signals for driving a display device which displays relative impedance changes. Like the impedance bridge technique, an output signal is provided which is proportional to a change in probe impedance, but it is difficult to map an actual impedance value back to a known defect.

An additional problem with both impedance bridge and qaudrature synthesis techniques is that a nulling circuit is required to each, which adds to the circuit complexity and provides additional circuitry which may affect the results and the reliability thereof.

Still further, it is difficult to use the balanced bridge and quadrature synthesis techniques with a plurality of probes, or with probes operating at different frequencies, and the speed with which relative impedance values are determined is rather slow. For different probes, it is even slower as rebalancing for each probe is required.

SUMMARY OF THE INVENTION

The foregoing shortcomings with conventional eddy current non-destructing testing methods and systems are resolved by the present invention which provides a digital system for determining absolute probe impedance values in magnitude and phase angle from probe signals. The impedance calculation is more accurate than is obtainable with a balanced brige or quadrature synthesis technique and the acquisition of impedance data occurs at a much faster rate than is possible with either.

In addition, the invention provides a system which can be used with multiple probes or with one probe operation at several different frequencies, thereby providing additional flexibility. The invention can accurately obtain impedance measurements with non-sinusoidal and aperiodic driving signals and it is not restricted to single frequency or sinusoidal driving signals. It is also possible to acquire data from other non-eddy current probes at high speed and store such data in correlation with eddy current data to provide even more meaningful information concerning detected flaw conditions.

Accordingly, one object of the present invention is to provide a digital eddy current measurement system which is capable of rapidly acquiring and storing data and for calculating absolute probe impedance values therefrom.

An additional object of the invention is to provide a digital eddy current measurement system which dispenses with the usual requirements for balancing and nulling circuits.

An additional object of the invention is to provide a digital eddy current measurement system in which acquisition of data is performed substantially independently of the analysis of the acquired data so that both data acquisition and analysis can occur at much faster rates.

These and other objects, advantages and features of the invention are obtained in a non-destructive eddy current measuring system which provides an eddy current measuring probe with a driving signal and which produces a signal representing the instantaneous current through the coil from the driving signal. A signal received from the probe representing the instantaneous voltage thereacross is also produced and both the current representing and voltage representing signals are converted to digital signals from which the magnitude and phase angle of the complex impedance of the probe is directly determined.

The conversion of the signals representing probe current and voltage into digital form and the storage thereof is performed by an input data acquisition system, while the analysis of the stored data is performed by a computer processor, with the input data acquisition system and computer processor operating largely independently of one another, in order to increase the speed and data acquisition and processing.

The invention will be better understood from the following detailed description which is provided in connection with the accompanying drawings.

DETAILED DESCRIPTION OF THE DRAWINGS

FIGS. 1A, 1B and 1C form a block diagram of the system of the invention;

DETAILED DESCRIPTION OF THE INVENTION

The present invention calculates a magnitude and phase angle of a complex impedance of a electromagnetic probe used in an eddy current measuring system. The impedance magnitude is calculated directly based on digital values representing probe current and voltage signals, while the phase angle of the complex impedance is measured by determining the time difference between the probe driving signal and a received signal therefrom.

Figure 3:
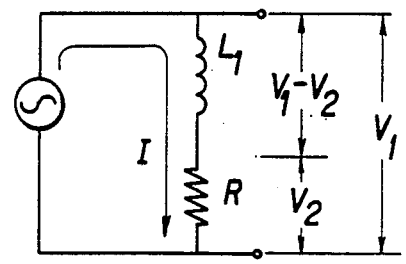
FIG. 3 is an equivalent circuit showing the method employed in the invention for calculating the magnitude of a probe impedance.

The technique used in the invention to calculate the magnitude of the complex impedance is best explained in conjunction with the FIG. 3 equivalent circuit of an eddy current probe. The probe electromagnetic coil is illustrated as $L_1$, while a known reference resistance value R is shown in series with the coil. A driving signal from source S is applied to the serial connection of the coil $L_1$ and resistance R. This produces voltage values $V_1$ and $V_2$ respectively across the serial interconnection of the coil $L_1$, and resistance R, and across the resistance R only. The current I in the probe coil $L_1$ is determined by dividing the voltage $V_2$ by the reference resistance value R, i.e., $I = V_2/R$ while the magnitude $|Z|$ of the complex impedance is determined by dividing the voltage across the coil $(V_1 - V_2)$ by the current value I, i.e., $$Z = \frac{(V_1 - V_2)}{I} = \frac{R(V_1 - V_2)}{V_2}$$

In the invention the voltage values $V_1$ and $V_2$, representing probe voltage $(V_1 - V_2)$ and current $V_2/R$ are acquired and digitized to provide stored digital waveforms representing these values which are used to calculate probe impedance.

Figure 1A:
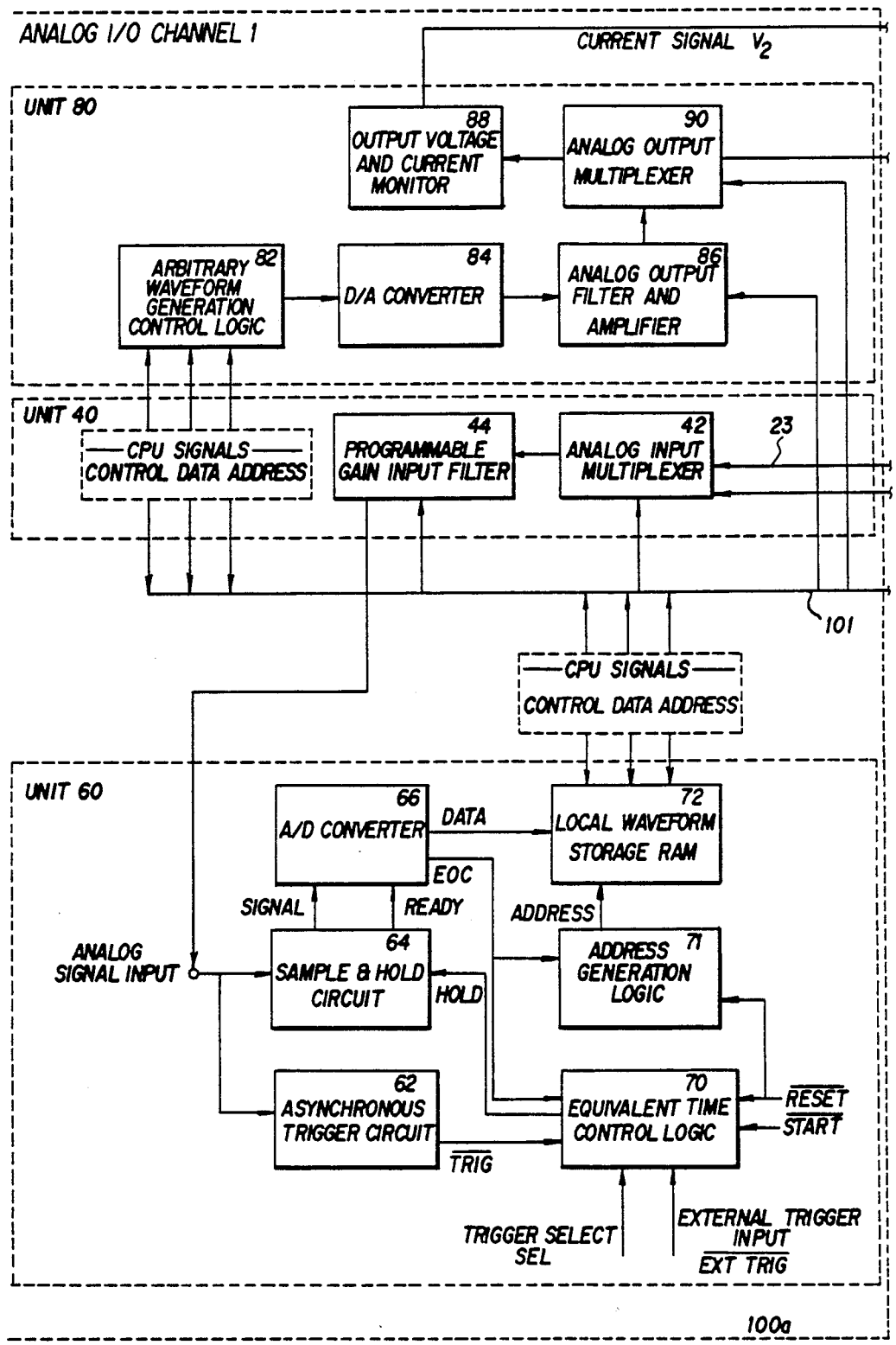
Figure 1B:
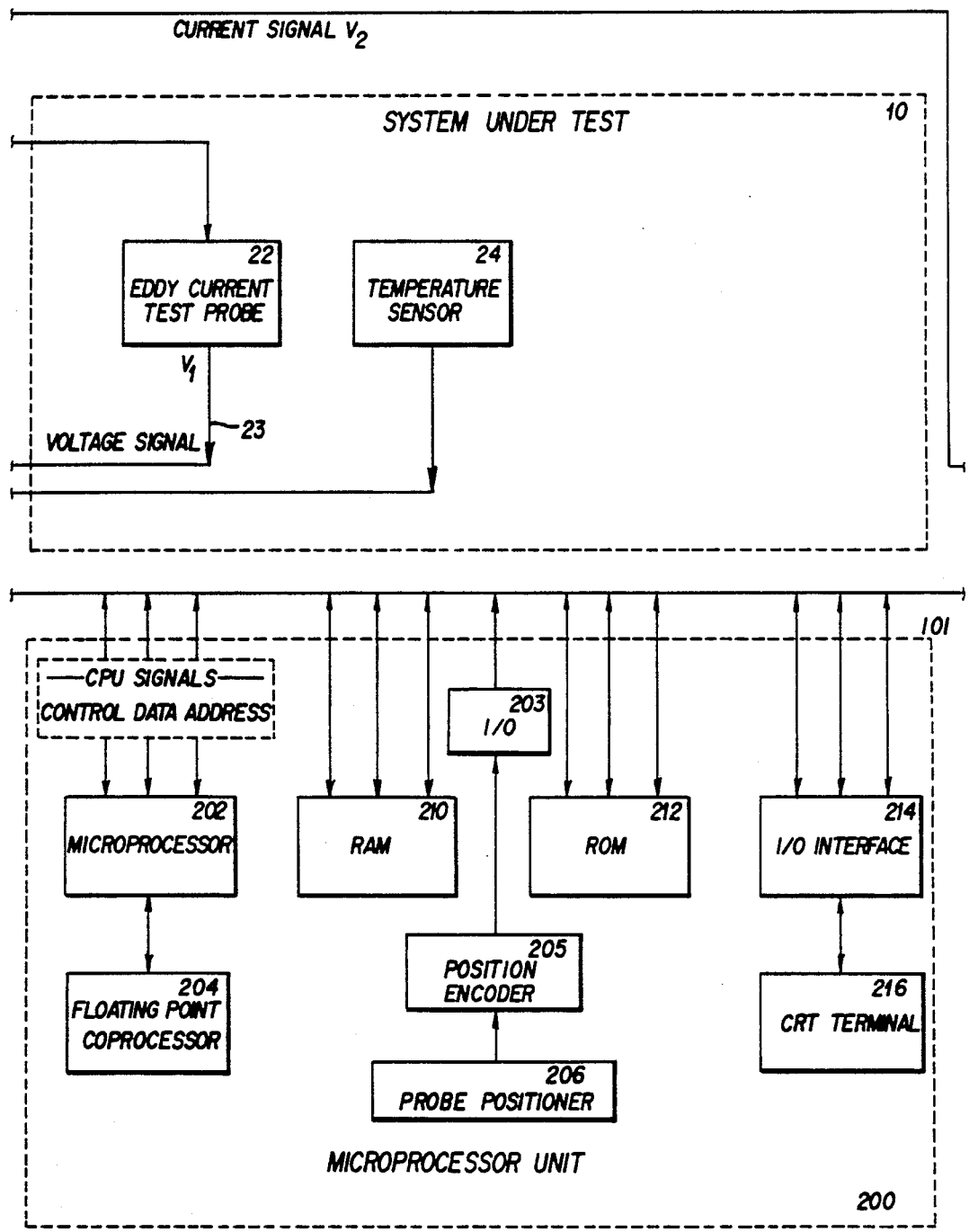
Figure 1C:
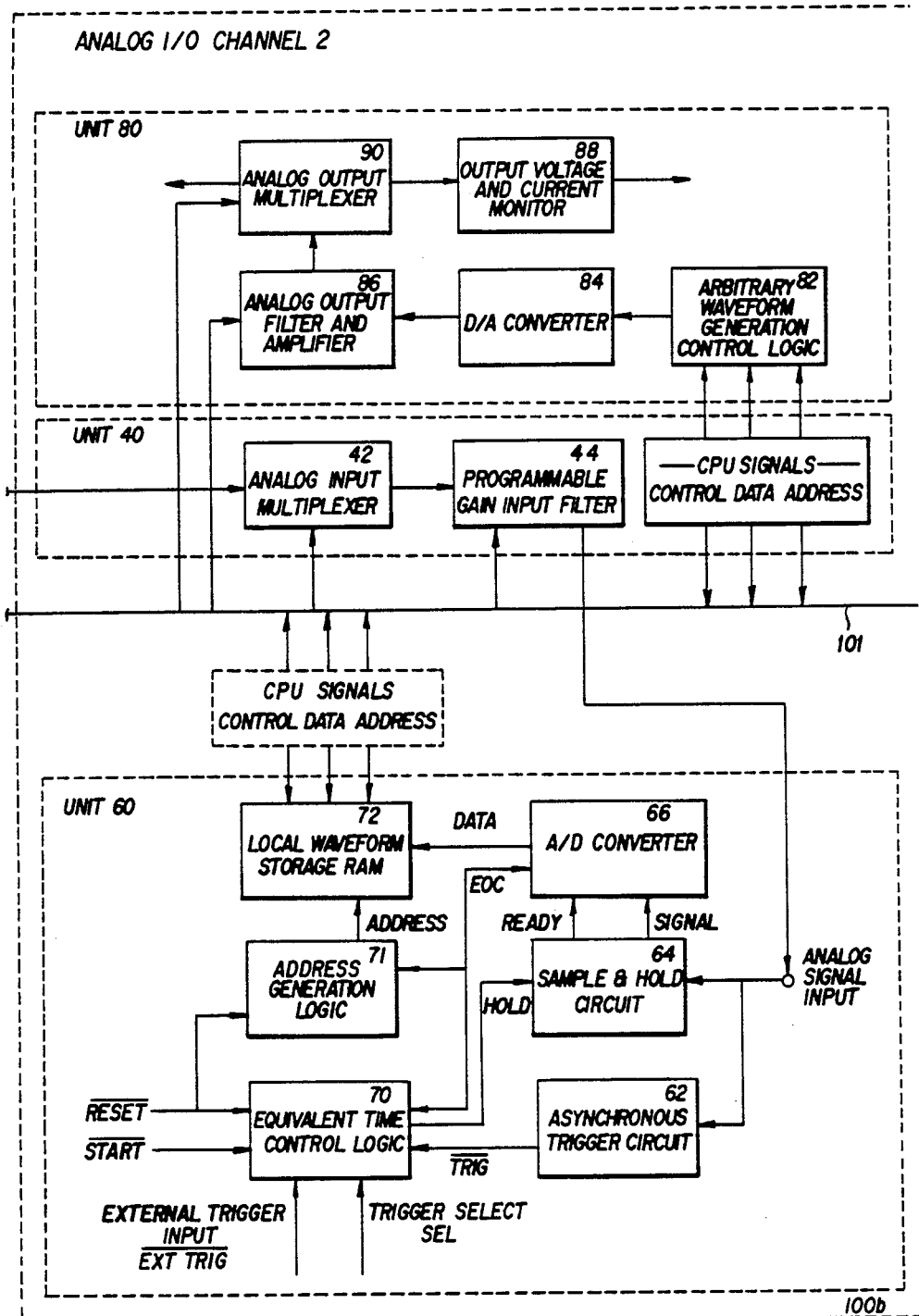

The overall digital eddy current measuring system of the invention is illustrated in FIG. 1. It is composed of two basic subsystems, a microprocessor unit 200, and a plurality of input-output channels 100a, 100b, ... communicating via a data and address bus 101 with the microprocessor unit 200. Two such input-output channels 100a and 100b are shown in FIG. 1, but it should be understood that many more than two channels can be used. Each of the input-output channels 100a, 100b, ... includes a data acquisition and storage unit 60, an analog input unit 40, and an analog output unit 80. To simplify description of the invention, only a single I/O channel 100a will be described in detail below. However, two such channels 100a and 100b are used to carry out the invention, the channel 100a being used to generate a probe driving signal and to acquire and store the voltage signal $V_1$, and the channel 100b being used to acquire and store the voltage signal $V_2$.

Actual communication with the eddy current probe 22 is made through the analog input unit 40 and the analog output unit 80 of channel 100a and through the analog input unit 40 of channel 100b. The analog output unit 80 of channel 100a provides the driving signal to the test probe 22, while the analog input unit 40 of channel 100a receives on line 23 the voltage signal $V_1$ at one input to multiplexer 42. The voltage signal $V_2$ from the output voltage and current monitor 88 of channel 100a is provided to the input of multiplexer 42 of channel 100b. As the test probe 22 is moved relative to a material under test, varying voltage signals $V_1$ and $V_2$ are produced for each impedance measuring point which are digitized, stored and analyzed by the system to provide complex impedance values, including magnitude and phase angle.

The manner in which the voltage signals $V_1$ and $V_2$ are acquired and stored will now be described. The analog input unit 40 of channel 100a includes an analog input multiplexer 42 which receives the output signal $V_1$ taken across the coil $L_1$ and reference resistor R (FIG. 3). This voltage $V_1$ is available at several locations, but for convenience is shown as taken from the output voltage and current monitor 88. This is the same signal supplied by multiplier 90 as the driving signal to the coil 22. In like manner, the analog input unit 40 of channel 100b receives at multiplexer 42 thereof the output signal $V_2$ from current monitor 88 for channel 100a. In addition to multiplexer 42, each analog input unit 40 also includes a programmable gain/attenuation input filter 44 which boosts or attenuates the output signal from multiplexer 42 to place it within a predetermined range of an A/D converter 66, and which applies microprocessor selectable low pass filtering characteristics to a signal at the output of filter 44.

The output of the programmable gain/attenuator filter 44 is provided as inputs to an asynchronous trigger generator circuit 62 and a sample and hold circuit 64 which are contained within the data acquisition and storage unit 60. Asynchronous trigger generator circuit 62 provides a trigger signal ($\overline{TRIG}$) at a predetermined point on a acquired voltage waveform, e.g., when a threshold level is exceeded. This trigger signal $\overline{TRIG}$ is supplied to a random equivalent time control logic ($\overline{RECTCL}$) circuit 70. As described in greater detail below, the equivalent time control logic circuit 70 responds to the presence of a $\overline{TRIG}$ signal, an end of conversion $\overline{EOC}$ signal from A/D converter 66, $\overline{RESET}$ and $\overline{START}$ signals from microprocessor 202, a trigger select ($\overline{SEL}$) signal, and an external trigger ($\overline{EXT\ TRIG}$) signal, and produces a series of "HOLD" signals to the sample and hold circuit 64 to initiate sequential sample and hold operations on an incoming analog signal. As a result, a digital sampling of the analog signal at the output of the programmable filter 44 occurs. The analog signal samples are then analog-to-digital converted by A/D converter 66 and the resultant digital values are sequentially stored in a waveform storage RAM 72 under control of address generation logic 71. Repeated samplings of the analog signal entering channel 100a will result in a digital signal waveform being stored in local RAM 72 representing an acquired voltage signal $V_1$ from test probe 22.

While the voltage value $V_1$ is being digitized and stored in channel 100a, a digital signal waveform of the voltage signal $V_2$ from current monitor 88 of channel 100a, applied to multiplexer 42, of channel 100b, is likewise being digitized and stored in a RAM 72 of channel 100b.

The analog input multiplexer 42, and programmable gain/attenuation input filter 44 of each channel is under control of the microprocessor 202 in the microprocessor unit 200. Consequently, the gain/attenuation factor of an acquired input signal can be adjusted by the microprocessor 202 so that it is in a suitable range for conversion by A/D converter 66. Moreover, the cutoff frequency of filter 44 can be set by the microprocessor to minimize the effect of noise on the acquired signal.

The microprocessor 202 also controls the analog input multiplexer 42 of each channel to multiplex a plurality of probe 22 output signals, or other signals, during the digital acquisition cycle. However, the high speed sampling and digitization of an input analog signal to a channel 100n is conducted by the equivalent time logic circuit 70, so that the microprocessor 202 is not required to handle this function.

The microprocessor 202 also controls the generation of a driving signal (i.e., the signal S of FIG. 3) for the test probe 22. This is accomplished by loading a digital signal waveform into a RAM of an arbitrary waveform generation control logic circuit 82 of channel 100a. This digital signal is converted by a digital-to-analog converter 84 into an analog probe driving signal. Various filter characteristics and amplification values can also be applied by analog output filter and amplifier 86, under control of microprocessor 202, and the resultant analog signal is applied to an analog output multiplexer 90 from which it is applied to test probe 22. The output voltage and current monitor 88 for channel 100a also receives the probe driving signal from multiplexer 42 and provides the voltage signal $V_2$, representing the probe signal current, to the input of the analog input multiplexer 42 of channel 100b.

As noted earlier, the system is configured so that as the voltage signal $V_1$ is being sampled and digitized so too is the voltage $V_2$, representing probe current. As a result, instantaneous and simultaneous digital sampling and storage of analog signals representing probe coil voltage ($V_1-V_2$) and probe coil current ($V_2$) occurs.

The microprocessor unit 200 includes the microprocessor 202 which runs the operating system and application programs for the system. It in turn works in conjunction with a floating point co-processor 204. A conventional input/output interface 214 is also provided, which allows operator interaction with microprocessor 202 via a conventional input/output device, e.g., a CRT terminal unit 216 for entry of data, e.g., setting data for gain/attenuation characteristics, filter characteristics, driving signal parameters, etc.

The microprocessor 202 can also acquire coordinate data representing the instantaneous position of probe 22 relative to a specimen under test by sampling the output of an X-Y digital position encoder 205 connected to a probe positioning device 206 via bus 101 and I/O interface 208. As described below, this data can be used to correlate calculated probe impedance values with corresponding locations on a test specimen at which an impedance measurement is taken.

The microprocessor 202 also communicates with RAM 210 and ROM 212 via the system data and address bus 101. The RAM 210 contains working areas for the microprocessor 202 and the ROM 212 contains the operating system and application programs for the microprocessor 202. The microprocessor also communicates via bus 101 with each channel 100a, 100b, ..., etc. As a consequence, microprocessor 202 is capable of accessing data stored in a local RAM 72 of any I/O channel 100n. Because the data is acquired and stored in RAM 72 by the equivalent time control logic 70, rather than under direct control of microprocessor 202, data acquisition and storage for the various I/O channels 100n can be run at high speed separately from the data processing functions performed by microprocessor 202. This uncoupling of the data acquisition and processing functions provides for a very fast acquisition and analysis of data.

Figure 2:
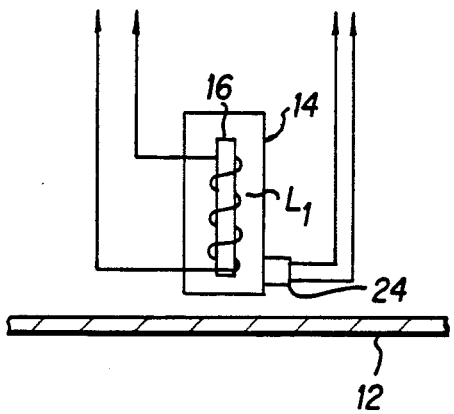
FIG. 2 is a schematic circuit of the probe used in the embodiment illustrated in FIGS. 1A, 1B and 1C.

FIG. 2 illustrates in schematic form the construction of an eddy current test probe 22 which may be used with the invention. The test probe includes a probe housing 14 containing an electromagnetic coil $L_1$ surrounding a magnetic core 16. An optional temperature sensing element 24 is mounted adjacent or within the housing 14. The output signal from the temperature sensing element 24 is provided to a respective input of the analog input multiplexer 42 of the I/O channel 100a. The output signal of temperature sensing element 24 is optionally used, as described below, to correct calculated impedance values in accordance with sensed temperature variations.

Returning to FIG. 1, input multiplexer 42 of each channel 100, under control of microprocessor 202, can also receive signals from other test or reference eddy current probes, other temperature sensors, or other types of probes which may detect or measure other characteristics of an object or material under investigation.

The manner in which the sampling and digitizing of analog signals applied to an I/O channel 100n is controlled by the random equivalent time control logic circuit 70 will now be described. The construction of this device is shown in greater detail in FIG. 4. Essentially the equivalent time control logic circuit 70 generates a series of HOLD signals at the output of NAND gate 75 which are applied to sample and hold circuit 64 to cause a sample of the analog signal from filter 44 to be held and then digitized by A/D converter 66. The HOLD signals are generated in response to internal generated sampling signals $\overline{INT}$ or external sampling signals $\overline{EXT\ TRIG}$ supplied to circuit 70 as HOLD signals from another like circuit 70 of another channel. A selection signal $\overline{SEL}$ applied to NAND gate 78 and inversely, via inverter 82, to NAND gate 77 controls whether the HOLD signals at gate 75 are generated in response to the $\overline{INT}$ signals supplied to gate 77 or the $\overline{EXT\ TRIG}$ signals supplied to gate 78, by selectively enabling either gate 77 or 78. The $\overline{SEL}$ signal can either be originated by microprocessor 202, or can be a hardwired switch signal.

Circuit 70 includes a programmable divider 81 for setting an internal clock rate (slave clock signal) from an externally applied system clock signal. Data for programming divider 81 is supplied thereto by microprocessor 202 through a latch circuit 83. The on-off state of the slave clock signal is controlled by an AND gate 91 which is, in turn, controlled by the Q outputs of flip-flops 85 and 87. Flip-flop 85 has a set input responsive to a $\overline{START}$ signal from microprocessor 202 and a reset responsive to a $\overline{RESET}$ signal from the microprocessor. Flip-flop 87 has its set input connected to receive the output of OR gate 113 which in turn receives respective end of conversion $\overline{EOC}$ and $\overline{TRIG}$ signals from A/D converter 66 and trigger circuit 62. The reset input of flip-flop 87 receives the output signal of AND gate 115 which, in turn, receives the signals $\overline{RESET}$ and $\overline{INT}$. With this arrangement, slave clock signals are started (gate 91 on) when a $\overline{START}$ signal is received from microprocessor 202, and one of the $\overline{EOC}$ and $\overline{TRIG}$ signals is generated by the A/D converter 66 or trigger circuit 62. They are stopped when a $\overline{RESET}$ from microprocessor 202 occurs or the signal $\overline{INT}$ is generated. The manner in which the signal $\overline{INT}$ is generated is described below.

The slave clock signals are supplied to a sample timing countdown counter 99. Counter 99 also receives as latched-in data, the output of a master counter 117 and counts down from the latched-in data until counter 99 has a count of zero which causes generation of the $\overline{INT}$ signal. The $\overline{INT}$ signal also causes counter 117 to increment by 1 and the new count value to be loaded into counter 99 via the load (L) input. Thus, as master counter 117 increments upwardly, an increasing number of slave clock signals are required to generate the $\overline{INT}$ signal. Thus, the successive $\overline{INT}$ signals are progressively delayed from the beginning of a cycle of a sampled analog signal to produce successive time spaced sampling HOLD signals at the output of gate 75. The successive $\overline{INT}$ signals will continue to increment counter 117 upwardly until counter 117 is reset via AND gate 107 which receives the signals $\overline{CMPEST}$ from a comparator 105, or $\overline{RESET}$ from microprocessor 202. The $\overline{CMPEST}$ signal is generated by comparator 105 whenever the count value in counter 117 coincides with a predetermined sample number limit data (predetermined number of HOLD signals to be generated) from the microprocessor 202 which is loaded into latch 103. Counter 117 is thus reset whenever a predetermined number of sampling signals $\overline{INT}$ have been generated as set in latch 103, indicating the end of a sampling cycle.

Initially, the circuit 70 (FIG. 1) is activated and the first HOLD signal generated by the $\overline{TRIG}$ signal received at gate 113. When the first HOLD signal is accordingly generated by occurrence of the $\overline{INT}$ signal, further slave clock signals are arrested at gate 91 because flip-flop 87 is then reset by the $\overline{INT}$ signal. Thereafter further HOLD signals are generated when flip-flop 87 is set by an end of conversion ($\overline{EOC}$) signal received from A/D converter 66 for each sampling which occurs and the $\overline{TRIG}$ signal from the asynchronous trigger circuit 62.

The random time equivalent logic circuit is reset at the end of each digitizing cycle by $\overline{CMPEST}$ or whenever microprocessor 202 issues a $\overline{RESET}$ signal. Once activated by the $\overline{START}$ signal from the microprocessor 202 and the $\overline{TRIG}$ signal from trigger circuit 62, the random time logic circuit 70 controls the acquisition of digital samples of an incoming analog signal and storage of those samples in local waveform storage RAM 72, thereby freeing microprocessor 202 to perform other tasks, such as analyzing previously acquired data.

Since the invention simultaneously digitizes the signals $V_1$ and $V_2$ in respective channels 100a and 100b, the equivalent time control logic 70 of channel 100b may be externally triggered off the $\overline{EXT\ TRIG}$ input thereto which is connected to the HOLD output of control logic 70 of channel 100a.

Figure 5:
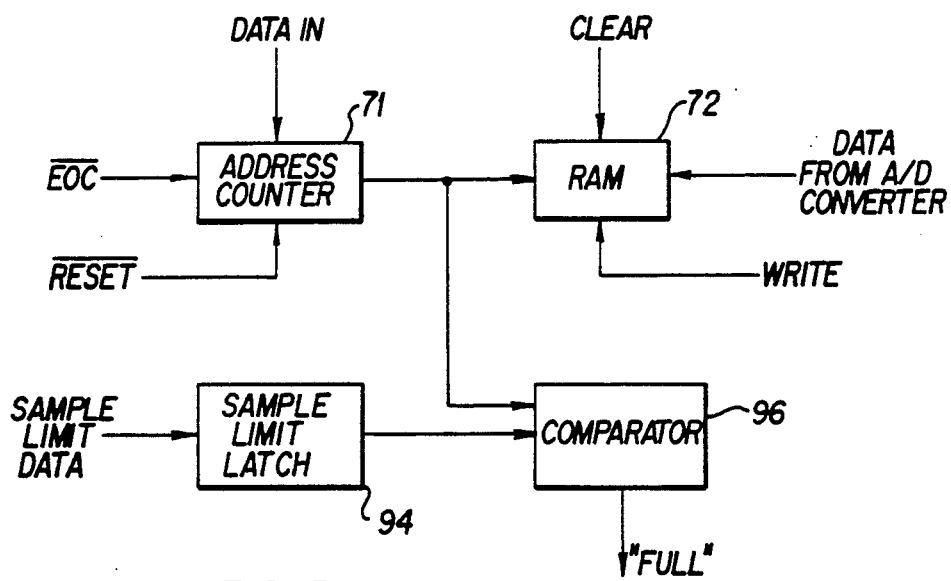
FIG. 5 is a block diagram showing in greater detail a RAM and associated addressing circuit employed in FIGS. 1A and 1C.

The RAM circuit 72 and associated address generation logic 71, are illustrated in greater detail in FIG. 5, which also shows associated support circuitry. As shown, RAM 72 receives the data input from the analog-to-digital converter 66 as well as a WRITE input from the A/D converter 66 which causes RAM 72 to read in the data from the A/D converter 66. Address input to the RAM 72 is supplied by an address generation logic 71 in the form of a counter which is incremented in response to the end of conversion $\overline{EOC}$ signal received from the A/D converter 66. Thus, as each new sample of data from A/D converter 66 is supplied to RAM 72, address counter 71 causes it to be loaded in the next sequential address location. The output of address counter 71 is also applied to a comparator 96 which receives as its other input the output of a sample limit latch 94. Microprocessor 202 loads a value into the sample limit latch 94 to control the number of samples of each waveform which are acquired and stored in RAM 72. When the address counter 71 output coincides with the data in the sample limit latch 94, comparator 96 provides a "full" output signal to the microprocessor 202 indicating that a waveform has been digitized and stored and is ready for acquisition by the microprocessor. The microprocessor 202 then moves the stored waveform from RAM 72 to RAM 210 for subsequent processing. The microprocessor in turn sends out a $\overline{RESET}$ signal to reset the random time equivalent logic circuit 70 and the address counter 71 in preparation for the next digitizing cycle.

Figure 6:
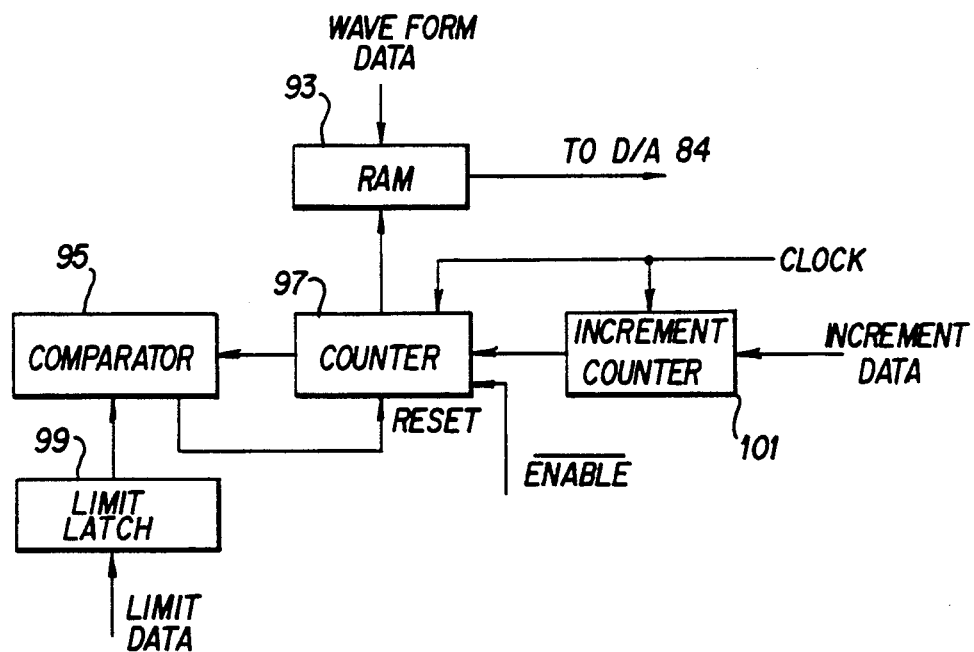
FIG. 6 is a block diagram showing in greater detail an arbitrary waveform generation logic circuit employed in FIGS. 1A and 1C.

As noted earlier, microprocessor 202 also supplies a digital waveform to the arbitrary waveform generation control logic 82 for generation of the driving signal for the eddy current probe 22. The arbitrary waveform generation control logic is shown in greater detail in FIG. 6. It includes a RAM 93 in which an arbitrary waveform is loaded by the microprocessor 202. The microprocessor 202 can supply one of a plurality of waveforms previously stored in ROM 212, or can generate a new waveform as configured by an operator entering data in terminal 216. In either case, the digital waveform is supplied to RAM 93. The digital waveform values stored in RAM 93 are then supplied to a digital-to-analog converter 84 in sequential order by the output of an address counter 97. The output of address counter 97 is also supplied to comparator 95 which receives as another input the output of a limit latch 99. The microprocessor 202 sets a value in the limit latch 99 when a probe driving signal is to be generated. The microprocessor 202 also supplies an increment value to a counter 101, the purpose of which will be described later. The microprocessor 202, once it establishes all the necessary values in the arbitrary waveform generation control logic 82, also enables the same by supplying an $\overline{\text{ENABLE}}$ input to the address counter 97 causing it to respond to applied clock pulses to sequentially address different storage locations in RAM 93 causing the data therein to be read out to the D/A converter 84. When the address counter 97 reaches a predetermined value set by the latch 99, comparator 95 detects this and causes the address counter 97 to be reset in preparation of the next generation of the probe driving signal. The addresses supplied to RAM 93 may be all of the addresses in which data is located, or, optionally, the address data can be supplied in increments such as every two addresses, every three addresses, etc. The increment is controlled by the increment counter 101 which is loaded with data by the microprocessor 202. As this counter counts to the incremented value, it disables the address output of counter 97 selectively so that only predetermined incremental address outputs are supplied to RAM 93. As a result, all of or only a portion of the data samples for a waveform are supplied to D/A converter 84, as determined by the microprocessor 202.

Once the RAM 93 stored waveform is supplied to the D/A converter 84, the output thereof is then fed to an analog filter and amplifier 86 which the microprocessor 202 sets for desired gain and smoothing filter characteristics. The output of filter/amplifier 86 is then fed as the probe driving signal to the analog output multiplexer 90 and through this to the output voltage and current monitor circuit 88. The latter circuit contains the reference resistance value R (FIG. 3) and circuitry for generating the output voltage $V_2$ of the output voltage and current monitor circuit 88, which represents probe current, and which is in turn fed to the input multiplexer of channel 100b.

Figure 8:
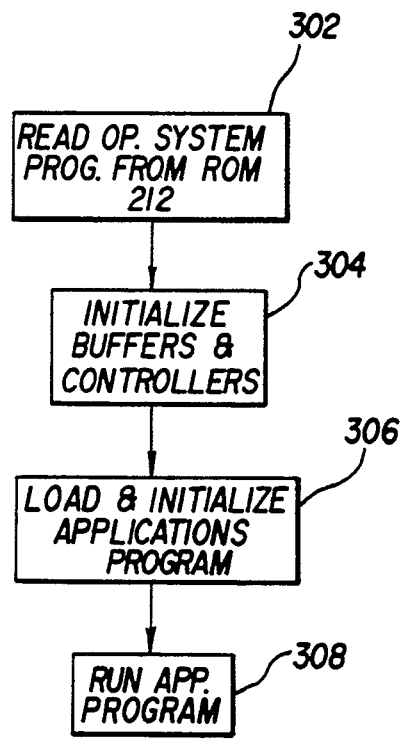
FIG. 8 is a flow chart depicting the initialization program used in the microprocessor illustrated in FIG. 1B.
Figure 9A:
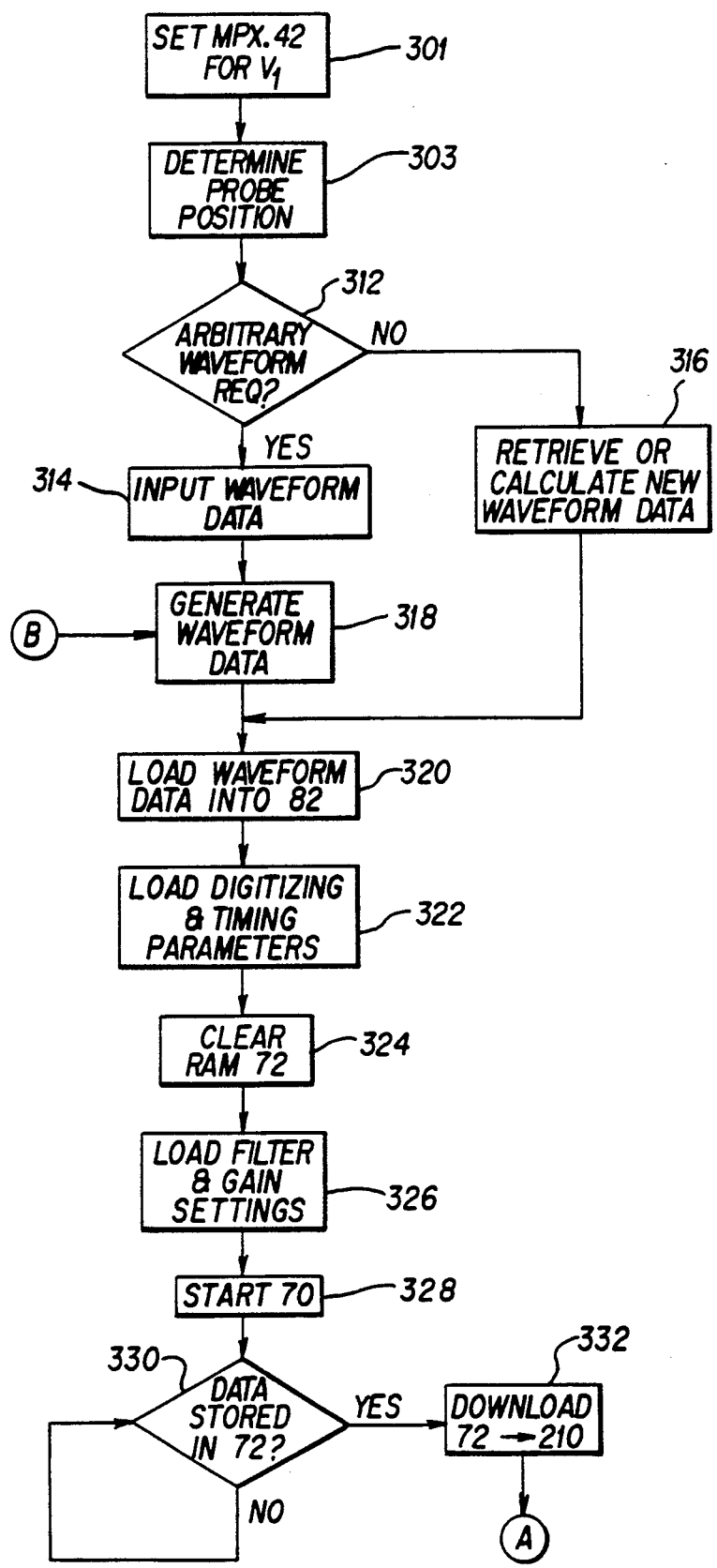
FIGS. 9A, 9B are flow charts depicting the main applications program run by the microprocessor.
Figure 9B:
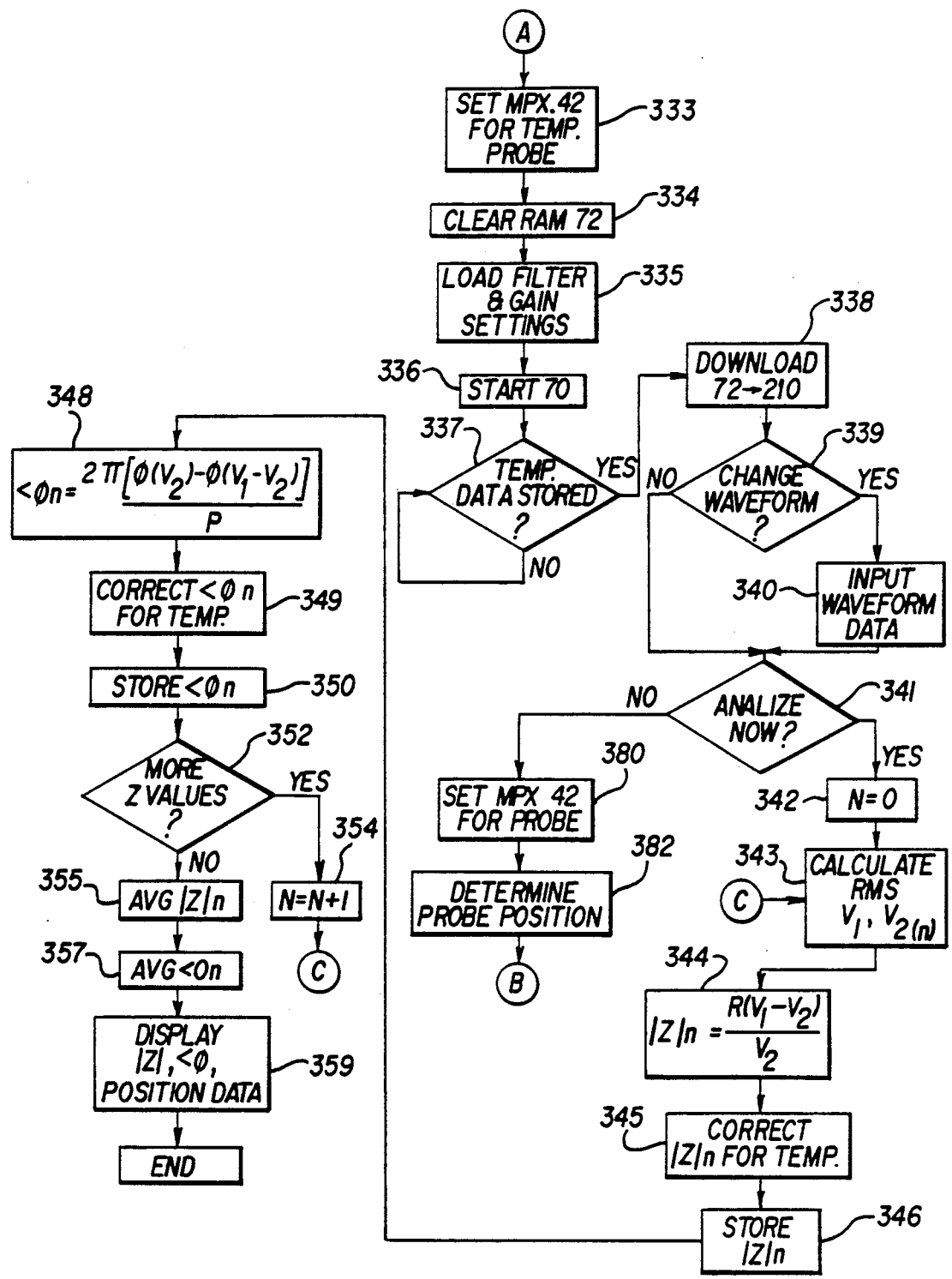

The microprocessor 202 performs its control and data analysis operations under control of the programs illustrated in FIGS. 8 and 9. FIG. 8 illustrates the initialization and start-up routines wherein in step 302 the microprocessor 202 executes a boot routine for loading the operation system program from ROM 212 into RAM 210. Once this is done, the microprocessor initializes various buffer registers and controller variables in step 304. It then loads the applications software from ROM 212 into RAM 210 and initializes various variables within the software in step 306. The application program is then run in step 308. The applications program for acquisition and analysis of data is shown in FIGS. 9A and 9B.

As a first step 301 in the application program the multiplexer 42 is set for the probe to be driven and in step 303 a probe position for the probe to be driven is determined by reading the X-Y coordinate data from position encoder 205. Then, a waveform for a probe driving signal is determined. In step 312 the microprocessor 202 determines whether an arbitrary waveform requested by an operator, or one calculated or stored by the microprocessor itself is to be used as the probe driving signal. If no arbitrary waveform is requested in step 312 the microprocessor proceeds to step 316 where it either generates a stored waveform pattern, e.g., a sine wave, either by retrieving one from memory, or by calculating one. The microprocessor determines the amplitude, shape and frequency of a driving signal. If in step 312 an arbitrary waveform is requested by an operator, then the microprocessor proceeds to step 314 where the operator inputs waveform data through CRT terminal 216 which the microprocessor 202 then uses in step 318 to generate a digital waveform for the probe driving signal.

Figure 4:
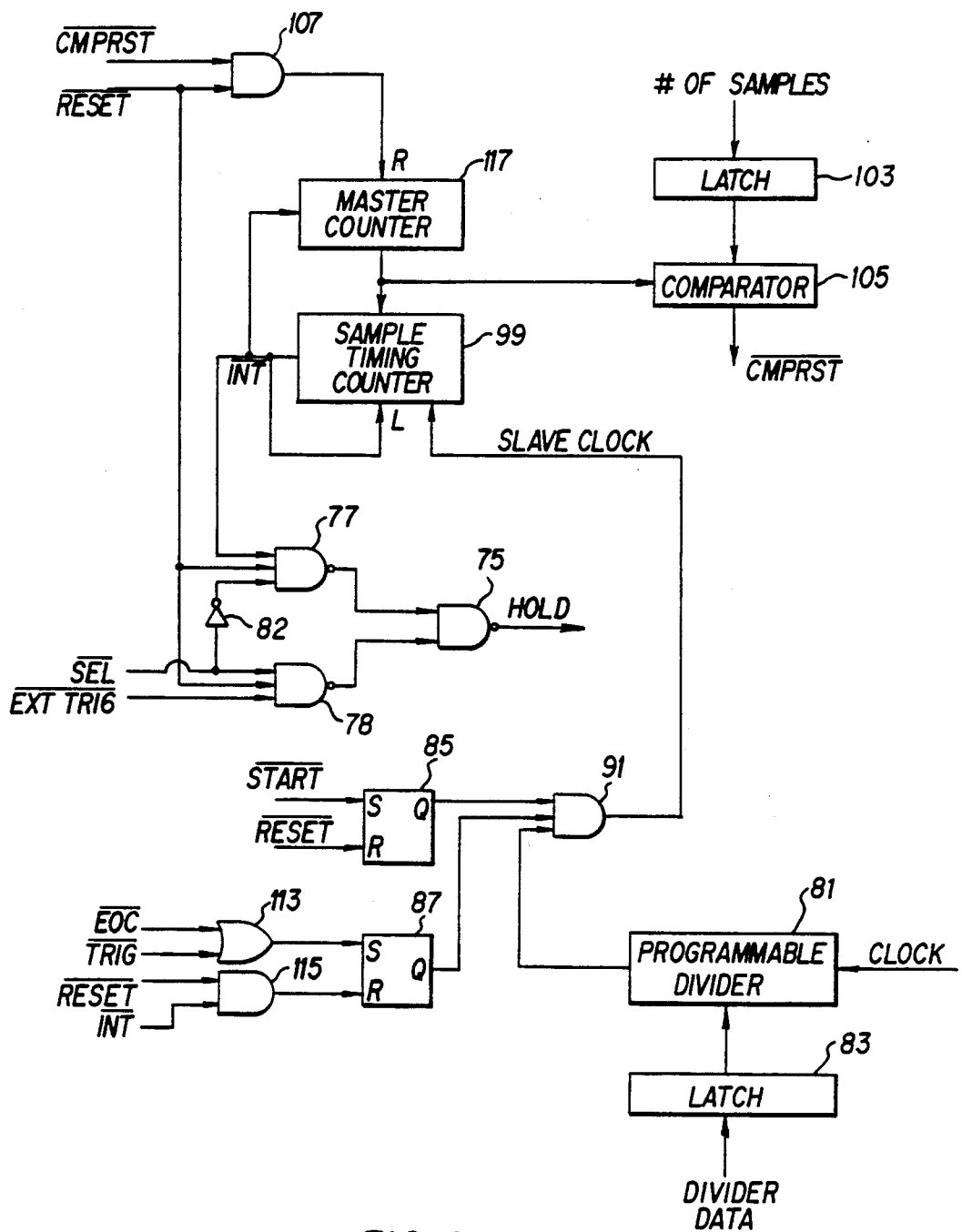
FIG. 4 is a more detailed block diagram of the equivalent time logic circuitry employed in FIGS. 1A and 1C.

From step 318 the microprocessor proceeds to step 320 where it loads the digital waveform into the arbitrary waveform generation control logic 82. Following this, in step 322, the microprocessor 202 loads digitization and timing data in the latches 83, 94, 99 and 103 and in counters 71 and 101 and then in step 324 clears the RAM 72. The microprocessor then, in step 326 loads gain/attenuation and filter settings into the programmable filters 44 and 86. Following this, in step 328 the microprocessor instructs the random equivalent time control logic circuitry 70 to begin data acquisition by sending it a $\overline{\text{START}}$ signal (FIG. 4).

The microprocessor 202 then sits in step 330 until RAM 72 indicates that an analog waveform has been digitized and loaded therein under control of the equivalent time control logic circuit 70 (FIG. 5 "FULL" signal). Actually, in step 330, the microprocessor is performing other tasks as it awaits the "FULL" signal which acts as a microprocessor interrupt signal. When the FULL signal is received, the microprocessor proceeds to step 332 where it moves the data in RAM 72 to RAM 210. The microprocessor 202 then begins to acquire a temperature value from temperature sensor 24 by setting, in step 333, multiplexer 42 to pass the output of the sensor 24 to the sample and hold circuit 64. After RAM 72 is cleared in step 334, and gain and filter settings loaded in step 335, the equivalent time control logic circuit 70 is then started in step 336 to commence digitization and storage of the temperature signal. When all samples of the sensor 24 are stored, as determined in step 337, the microprocessor downloads RAM 72 into RAM 210 in step 338 and then determines, in step 339, whether a different probe driving signal is desired by an operator. If a new driving signal waveform is desired, waveform input parameters are accepted from an operator in step 340. Following this, or if no waveform change is desired as detected in step 339, the microprocessor proceeds to step 341 where it determines if previously acquired waveform data should now be analyzed. If the answer is no, the microprocessor sets the multiplexer 42 for a desired probe in step 380 and then determines new probe coordinate position data in step 382 returns to step 318 where it generates waveform data and begins the sequence for generating a new probe driving signal.

If in step 341, the microprocessor determines that previously acquired data is to be analyzed, it begins that analysis. The first step of this analysis is to set a counter N to zero as illustrated in step 342. Then the RMS values of the digital sample (n) of waveforms $V_1$ and $V_2$ are calculated in step 343. Then, in step 344, the current value $I = V_2/R$ and impedance magnitude $$|Z| = \frac{V_{\text{probe}}}{I_{\text{probe}}} = \frac{(V_1 - V_2)}{I} = \frac{R(V_1 - V_2)}{V_2}$$

is determined for pairs of samples $V_1$ and $V_2$. Once the absolute magnitude $|Z|_n$ of the complex impedance is calculated, the microprocessor proceeds to step 345 where it corrects a calculated $|Z|_n$ value in accordance with previously acquired temperature data, described below and then stores in step 346 the corrected value $|Z|_n$ together with probe position data associated with the measured impedance value, following which it calculates the phase angle $<\phi_n$ in step 348.

The phase angle $<\phi_n$ is determined by finding the same reference point, e.g., a zero crossing point, on the probe voltage ($V_1-V_2$) signal and the signal $V_2$ representing current through the coil L1, and determining the time difference between these two reference values, dividing this time difference by the period P of the signal and multiplying the result by the value $2\pi$. This produces the phase angle $<\phi_n$ of the complex impedance, which is corrected for temperature variations in step 349 and stored in step 350 with corresponding probe position data. Once this is done the microprocessor has an impedance value in the form of an absolute magnitude $|Z|_n$ and phase angle $<\phi_n$ for respective sample points n of the received waveforms $V_1$ and $V_2$ for an associated probe position. After storing the phase angle $<\phi_n$ value together with associated probe position data in step 350, the microprocessor then determines in step 352 if there are more $|Z|_n$ values to be obtained, that is, if there are more data samples n in the waveform data sets to be analyzed. If there are, the microprocessor increments the N counter in step 354 and then proceeds back to step 343 where it analyzes the next pair $V_1$, $V_2$ and begins the processing sequence again to calculate the next impedance value. Once all impedance values (absolute magnitude and phase) for the acquired $V_1$, $V_2$ waveforms have been obtained and stored, and RAM 210 contains impedance waveforms as absolute magnitude and phase angle waveforms. When the microprocessor determines in step 352 that all impedance values have been processed, it proceeds to step 355 where it averages all magnitude values $|Z|_n$ and to step 357 where it averages all phase angles $<\phi$ for a given measuring point. After this, the microprocessor displays, in step 359, the averaged values of $|Z|_n$ and $<\phi_n$ in association with probe position data on the CRT terminal 216 or other output device and the program then ends.

As noted, each of the absolute impedance and phase angle values $|Z|_n$, $<\phi_n$ determined in steps 344 and 348 may be corrected in accordance with the temperature data acquired in step 335. Correction may be accomplished by multiplying each of the determined values $|Z|_n$ and $<\phi_n$ by respective coefficients a and b which are stored in a look-up table beforehand by microprocessor 202 in association with various possible detected temperature values. The microprocessor determines the values a, b from the digitized temperature values acquired in step 335 and uses them to correct the calculated $|Z|_n$ and $<\phi_n$ values in steps 345 and 349.

While any one of the pairs $|Z|_n$ and $<\phi_n$ can be used as the complex impedance of a measuring point, it is preferred that all of the values $|Z|_n$ for a sampling cycle be averaged to produce the magnitude of the complex impedance, and all of the values $<\phi_n$ for a sampling cycle be averaged to produce the phase angle $<\phi$, as illustrated by steps 355 and 357 and then the averaged $|Z|$ and $<\phi$ values displayed in step 359 on CRT terminal 216 together with the acquired position data.

As seen from the above, the invention provides a digital eddy current measurement system which is capable of directly calculating the absolute magnitude $|Z|$ and phase angle $<\phi$ value of the complex impedance at the probe by using probe current and voltage values directly. The system does not require impedance bridge circuits, or quadrature synthesis circuitry or time consuming calibration steps. In addition, no nulling circuits are required and an extremely fast acquisition of eddy current data is made possible as the digital sampling of input data is under control of an equivalent time control logic 70. Moreover, since probe current and voltage are directly measured and used to calculate the complex impedance, additional errors introduced by circuitry which indirectly measures these values are avoided.

Still further, since the system is entirely digital, and capable of generating several different driving signals at several different multiplex outputs, and also capable of accepting several different multiplexed input signals from different probes, whether eddy current probes or not, the system is readily adaptable for use with probes energized by multiple frequency driving signals. In the system of the invention, each frequency signal can be separately processed and analyzed, and as each input signal is received, appropriate filter characteristics and gain/attenuation characteristics can be applied to readily match the signal to the digitizing capability of A/D converter 66.

The system not only handles eddy current probes, but many other types of probes can also be used to provide additional data in, for example, a flaw detection environment. For example, the system can also be used with ultrasonic probes, temperature probes, pressure probes, spring probes, compliance probes, photodiodes, photomultiplier tubes, capacitor probes and microwave probes, the data outputs of which can be digitized and stored in the system in conjunction with probe impedance data.

Figure 7:
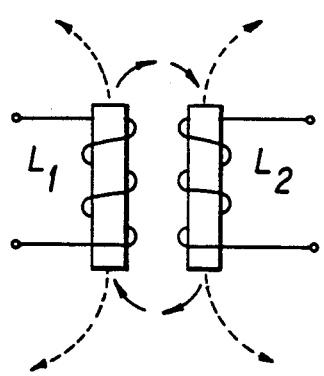
FIG. 7 illustrates an embodiment of a probe having two coils which may be energized in phase or out of phase.

An additional aspect of the system is illustrated in connection with the probe shown in FIG. 7. FIG. 7 illustrates a dual coil eddy current probe in which two coils are provided in parallel alignment. The two driving signals for the probes can be applied from respective I/O channels 100n in-phase or out-of-phase to achieve different depth of penetration effects. To do this steps 312 to 320 of FIG. 9A are modified to load respective driving signals into the arbitrary waveform generation control logic 82 of two separate channels. When the probe signals are applied in phase, the flux between the two probe coils provides a deep penetration into an object. With the probes energized out of phase, a more localized surface inspection of an object is created as the magnetic field generated by the probes moves in a direction away from between the two probe cores. This type of probe can be particularly uniquely used in the invention to provide surface impedance data and depth impedance data.

We claim:

1. An eddy current measuring system comprising:
   an eddy current measuring probe having an electromagnetic coil;
   a reference resistor connected in series with said electromagnetic coil for producing a reference resistor value;
   means for applying a first driving signal to said coil;
   means for producing second and third voltage signals respectively representing a probe current in said coil and a probe voltage across said coil, said second and third signals being produced during the time said driving signal is applied to said coil;

means for analog-to-digital converting said second and third signals;

means for determining a plurality of magnitude and phase angle values representing the complex impedance of said probe from said converted second and third signals; and storing means connected to said determining means for receiving and storing said plurality of magnitude and phase angle values from said determining means wherein said converted values from said second signals represent probe current values and said converted values from said third signals represent probe voltage values and for storing said reference resistance value received from said reference resistor and for providing said reference resistance value to said determining means;

wherein said means for determining produces a plurality of digital signal values representing probe current by dividing sample values of said second voltage signal by said reference resistance value wherein each said second voltage sample is represented by a voltage $V_2$ across said reference resistance R as $I=V_{2/R}$ and for producing a plurality of digital values representing said third voltage signal where each said third voltage value is represented by a voltage $(V_1-V_2)$, wherein $V_1$ is the voltage across a serial interconnection of said coil and said reference resistance, said voltages $V_1$ and $V_2$ being said voltage signals representative of the instantaneous current (I) through said coil and the instantaneous voltage $(V_1-V_2)$ across said coil.

2. A measuring system as in claim 1, wherein said means for determining the magnitude of said impedance determines RMS values for said voltage signals, said RMS values being used to produce a value representing the magnitude of the probe impedance.

3. A measuring system as in claim 1, wherein said stored digitized second signal represents probe current and wherein said means for determining phase angle comprises means for producing a probe voltage signal from at least one of said stored digitized second and third signals, means for defining a first reference point on one of the stored digitized second and probe voltage signals, means for finding a corresponding reference point on the other of the stored digitized second and probe voltage signals, means for determining the time difference between the two reference points, means for dividing the time difference by the period of one of said stored digitized second and probe voltage signals and means for multiplying the result by $2\pi$.

4. A system as in claim 1, wherein said means for determining the magnitude of said impedance determines an RMS voltage value for said stored digital signals and uses the RMS voltage values to produce a value representing the magnitude of probe impedance.

5. A system as in claim 4, wherein said means for determining determines a plurality of impedance magnitude values from respective pairs of stored samples of said stored digital signals.

6. A measuring system as in claim 1, further comprising means providing coordinate data representing the instantaneous position of said probe relative to an object; and means for associating a determined magnitude and phase angle for said complex impedance with coordinate data representing the position of said probe at which said magnitude and phase angle were determined.

7. A measuring system as in claim 1, wherein said means for applying comprises:

means for creating a digital waveform, means for storing said digital waveform; and means for digital-to-analog converting said stored digital waveform into an analog probe driving signal.

8. A measuring system as in claim 7, wherein said creating means is able to change the shape, amplitude and frequency of said digital waveform.

9. A measuring system as in claim 1, further comprising at least one other probe for detecting a characteristic of said object, means for deriving a signal representing said object characteristic at a particular location of said object, and means for associating said signal representing said object characteristic at said particular location with a determined value of magnitude and phase angle for the complex impedance of said first probe for said location.

10. A probe impedance measuring system comprising:

a probe comprising an electromagnetic coil;

means for generating a probe driving signal;

means for applying said driving signal to said probe coil;

means for receiving signals representing a voltage across said coil and a current passing through said coil when said coil is driven by said driving signal;

means for sampling and analog-to-digital converting said signals representing coil voltage and coil current to produce digital samples of said signals representing coil voltage and current;

means for storing said digital samples;

control logic means for controlling the sampling and converting means to produce said digital samples; and processor means for controlling said generating means and applying means so that said driving signal is generated and applied to said probe coil, for initializing operation of said control logic means so that said signals representing coil current and coil voltage are converted to said digital samples, and for calculating a complex probe impedance from said stored digital samples of said signals representing coil voltage and current.

11. A system for directly measuring the magnitude and phase angle of a complex coil impedance comprising:

a probe comprising an electromagnetic coil;

a reference resistor connected in series to said electromagnetic coil for producing a reference resistor value;

a driving signal generator adapted to apply a probe driving signal to said coil;

means operative when said driving signal is applied to said coil for obtaining voltage signals representative of the instantaneous current through said coil and the instantaneous voltage across said coil;

analog to digital converter means for converting said voltage signals representative of instantaneous current through said coil and said instantaneous voltage across said coil respectively into first and second digital signals, each comprising a plurality of digital samples;

means for determining a value of a magnitude and phase angle of a complex impedance of said coil from said first and second digital signals, said means for determining a value of the magnitude and phase angle of said complex impedance doing so by extracting a plurality of sets of digital samples, one from each of said first and second digital signals, and using each said set of extracted digital samples to form a respective magnitude value and a respective phase angle value, thereby forming a plurality of magnitude and phase angle values corresponding to said plurality of sets of digital samples; and storing means connected to said determining means for storing said plurality of magnitude and phase angle values representing said first and second digital signals received from said determining means and for receiving and storing said reference resistance value and for providing said reference resistance value to said determining means;

wherein said determining means produces said second digital signals by dividing sample values of said second digital signal representing said probe current by said reference resistance value wherein each said probe current value is represented by a voltage $V_2$ across a reference resistance R as $I = V_{2/R}$ and said second digital signals are represented by a voltage $(V_1 - V_2)$, where $V_1$ is the voltage across a serial interconnection of said electromagnetic coil and said reference resistor, wherein said voltages $V_1$ and $V_2$ being said voltage signals representative of the instantaneous current (I) through said coil and the instantaneous voltage $(V_1 - V_2)$ across said coil.

12. A system as in claim 11, wherein one of said voltage signals represents instantaneous coil current and said means for determining said phase angle comprises: means for defining a first reference point on one of a) said voltage signals which represents instantaneous probe current and b) a signal formed from said voltage signals which represents the voltage across said probe coil, means for finding a corresponding second reference point on the other signal, and means for determining the time difference between the two reference points, for dividing the difference by the period of one of said signals, and for multiplying the result by $2\pi$.

13. A system as in claim 11, further comprising means providing coordinate data representing the position of said probe relative to an object; and means for associating a determined magnitude and phase angle for said complex impedance with coordinate data representing the position of said probe at which said magnitude and phase angle were determined.

14. A system as in claim 11, further comprising means for changing the characteristics of said probe driving signal.

15. A system as in claim 11, wherein said generator comprises:
means for creating a digital waveform,
means for storing said digital waveform; and
means for digital-to-analog converting said stored digital waveform into an analog probe driving signal.

16. A system as in claim 11, further comprising means for sensing a temperature and provided adjacent said probe, means for receiving an output signal from said temperature sensor, said means for determining the magnitude of said complex impedance correcting a determined magnitude value in accordance with the output of said temperature sensor.

17. A system as in claim 16, wherein said means for determining the phase angle of said probe impedance corrects a determined phase angle value in accordance with the output of said temperature sensor.

18. A system as in claim 11, further comprising at least one other probe for detecting a characteristic of said object,
means for deriving a signal representing said object characteristic at a particular location of said object, and
means for associating said signal representing said object characteristic at said particular location with a determined value of magnitude and phase angle for the complex impedance of said first probe for said location.

19. A system as in claim 15, wherein said creating means is able to change the shape, amplitude and frequency of said digital waveform.

20. A system as in claim 11, wherein said probe further comprises another coil positioned adjacent said electromagnetic coil, and said system further comprises means for generating a driving signal for said another coil which is either in phase or out of phase with said driving signal for said electromagnetic coil.

21. A system as in claim 11 further comprising:
means for forming an average magnitude value from a stored plurality of magnitude values; and
means for forming an average phase angle value from a stored plurality of phase angle values.

22. A system as in claim 11 further comprising means for acquiring additional probe data, said analog-to-digital converter means converting said additional probe data into a third digital signal and means for storing said third digital signal.

23. A system as in claim 22 wherein said additional probe data represents temperature data, said system further comprising means for correcting each of said plurality of magnitude and phase angle values by using said temperature data.

24. A system as in claim 11 wherein said pair of voltage signals are respectively taken from across said series connection and from across said reference resistance.

* * * * *

UNITED STATES PATENT AND TRADEMARK OFFICE
CERTIFICATE OF CORRECTION

PATENT NO.   :   5,055,784

DATED        :   October 8, 1991

INVENTOR(S)  :   Douglas J. Jaeger and Howard P. Groger

It is certified that error appears in the above-identified patent and that said Letters Patent is hereby corrected as shown below:

Column 1, line 5, insert:

--This invention was made with Government support under N00019-85-C-0361 awarded by the Department of the Navy. The Government has certain rights in this invention.--.

Signed and Sealed this

Fourth Day of November, 1997

Attest:

BRUCE LEHMAN

Attesting Officer

*Commissioner of Patents and Trademarks*